United States Patent [19]

Sugimori et al.

[11] Patent Number: 4,536,321

[45] Date of Patent: Aug. 20, 1985

[54] FLUOROBENZENE DERIVATIVES AND LIQUID CRYSTAL COMPOSITIONS CONTAINING THE SAME

[75] Inventors: Shigeru Sugimori, Fujisawashi; Tetsuhiko Kojima, Yokohamashi; Yasuyuki Goto, Yokohamashi; Toyoshiro Isoyama, Yokohamashi; Kazunori Nigorikawa, Yokohamashi, all of Japan

[73] Assignee: Chisso Corporation, Osaka, Japan

[21] Appl. No.: 580,628

[22] Filed: Feb. 16, 1984

[30] Foreign Application Priority Data

Feb. 18, 1983 [JP] Japan .................................. 58-25689
Mar. 15, 1983 [JP] Japan .................................. 58-42992
Mar. 28, 1983 [JP] Japan .................................. 58-52179
Apr. 18, 1983 [JP] Japan .................................. 58-68188

[51] Int. Cl.³ .......................... C09K 3/34; G02F 1/13; C07C 121/64; C07C 49/807; C07C 49/813
[52] U.S. Cl. ............................ 252/299.63; 252/299.5; 350/350 R; 350/350 S; 260/465 F; 260/465 G; 568/329; 568/331
[58] Field of Search ...................... 252/299.63, 299.66, 252/299.5, ; 350/350 R, 350 S; 260/465 F, 465 G; 568/329, 331

[56] References Cited

U.S. PATENT DOCUMENTS

| 4,130,502 | 12/1978 | Eidenschink et al. | 252/299.63 |
| 4,154,697 | 5/1978 | Eidenschink et al. | 252/299.63 |
| 4,302,352 | 11/1981 | Eidenschink et al. | 252/299.63 |
| 4,382,012 | 5/1983 | Eidenschink et al. | 252/299.63 |
| 4,400,293 | 8/1983 | Römer; et al. | 252/299.63 |
| 4,405,488 | 9/1983 | Sugimori et al. | 252/299.63 |
| 4,415,470 | 11/1983 | Eidenschink et al. | 252/299.63 |
| 4,422,951 | 12/1983 | Sugimori et al. | 252/299.63 |
| 4,439,340 | 3/1984 | Kojima et al. | 252/299.63 |
| 4,472,293 | 9/1984 | Sugimori et al. | 252/299.63 |
| 4,478,740 | 10/1984 | Eidenschink et al. | 252/299.62 |
| 4,490,305 | 12/1984 | Eidenschink et al. | 252/299.63 |

FOREIGN PATENT DOCUMENTS

| 19665 | 12/1980 | European Pat. Off. | 252/299.63 |
| 74608 | 3/1983 | European Pat. Off. | 252/299.63 |
| 84194 | 7/1983 | European Pat. Off. | 252/299.63 |
| 90671 | 10/1983 | European Pat. Off. | 252/299.63 |
| 3205766 | 8/1983 | Fed. Rep. of Germany | 252/299.63 |
| 3208089 | 9/1983 | Fed. Rep. of Germany | 252/299.63 |
| 3209178 | 9/1983 | Fed. Rep. of Germany | 252/299.63 |
| 3211601 | 10/1983 | Fed. Rep. of Germany | 252/299.63 |
| 59-16840 | 1/1984 | Japan | 252/299.63 |
| 59-42329 | 3/1984 | Japan | 252/299.63 |
| 2078727 | 1/1982 | United Kingdom | 252/299.63 |

OTHER PUBLICATIONS

Osman, M. A., et al., Mol. Cryst. Liq. Cryst., vol. 82 (Letters) pp. 331–338 (Jan. 1983).

*Primary Examiner*—Teddy S. Gron
*Attorney, Agent, or Firm*—Fred Philpitt

[57] ABSTRACT

Novel liquid crystal compounds having a large positive dielectric anisotropy value and also a low viscosity and a good stability to heat, light, air and water, and liquid crystal compositions containing the same are provided, which compounds are fluorobenzene derivatives expressed by the general formula

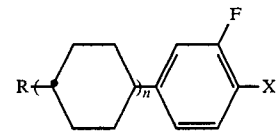

wherein n represents 1 or 2, X represents CN or $COCH_3$, and R represents hydrogen atom or an alkyl group or an alkoxy group each of 1 to 15 carbon atoms.

8 Claims, No Drawings

FLUOROBENZENE DERIVATIVES AND LIQUID CRYSTAL COMPOSITIONS CONTAINING THE SAME

BACKGROUND OF THE INVENTION

1. Field of the Invention

This invention relates to novel liquid crystal compounds having a positive dielectric anistropy, and liquid crystal compositions containing the same.

2. Description of the Prior Art

Liquid crystal display elements utilize optical anisotropy and dielectric anisotropy of liquid crystal substances, and are classified into various types such as TN (twisted nematic) type, DS (dynamic scattering) type, guest-host type, DAP type, White-Tailor type, etc. according to their display modes, and the properties of liquid crystal substances required for their respective uses are different. For example, liquid crystal substances having a positive dielectric anisotropy $\Delta\epsilon$ are required or those having a negative one are required or those having an intermediate value therebetween are suitable, depending on the kinds of display elements. Anyhow, however, in any mode, liquid crystal substances to be used are necessary to exhibit a liquid crystal phase in temperature ranges as broad as possible, around room temperature, and also to be stable to heat, air, light, etc. At present, however, no single compound which alone satisfies all such conditions is present, and it is the present status that several kinds of liquid crystal compounds or these compounds and non-crystalline compounds are mixed to obtain those which withstand practical uses for the present.

Recently, need particularly for liquid crystal display elements which can be driven at low voltages has increased, and in order to satisfy such a requirement, liquid crystal compositions having a larger $\Delta\epsilon$ value are usually required.

In general, liquid crystal compositions having an optional $\Delta\epsilon$ value can be obtaind by adequately mixing compounds having a positive $\Delta\epsilon$ value with those having a negative $\Delta\epsilon$ value. Thus, in order to obtain a liquid crystal composition having a large positive $\Delta\epsilon$ value, a component having as large a positive $\Delta\epsilon$ value as possible will be to be used. In this case, however, there should be used those which have a good compatibility with other components and extend the mesomorphic range of the resulting composition or at least do not narrow it. In order to satisfy such an object, the present inventors previously invented carboxylic acid 3-chloro-4-cyanophenyl esters expressed by the general formula

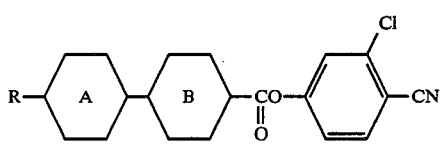

wherein R represents an alkyl group or alkoxy group of 1 to 10 carbon atoms and

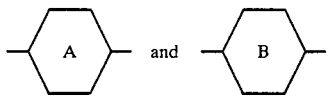

represents benzene ring or cyclohexane ring, and applied for patent (Japanese patent application laid-open No. Sho57-154158/1982). Recently, however, liquid crystal display elements having a higher level of performances have been needed, and compounds having a lower viscosity and a good stability to heat, light, air and moisture have been required. The present invention has been made to meet such a demand.

SUMMARY OF THE INVENTION

The present invention resides in fluorobenzene derivatives expressed by the general formula

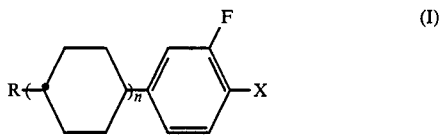

wherein n represents 1 or 2; X represents CN or COCH$_3$; and R represents H or an alkyl group or alkoxy group of 1 to 15 carbon atoms, and liquid crystal compositions containing the same.

DETAILED DESCRIPTION OF THE PREFFERED EMBODIMENTS

Particularly, compounds of the above general formula wherein X represents CN have a positive dielectric anisotropy value as large as about +30, a low viscosity for such value and a good stability to heat, light, air and water and exhibit a liquid crystal phase in a broad temperature range; hence they are suitable as components constituting a liquid crystal composition which has a large $\Delta\epsilon$ value, a low viscosity and a board mesomorphic range. More particularly, compounds of the general formula wherein X represents CN and n is 2, i.e. 3-fluoro-4-cyano-1-[trans-4-(trans-4-substituted cyclohexyl)cyclohexyl]benzene expressed by the general formula

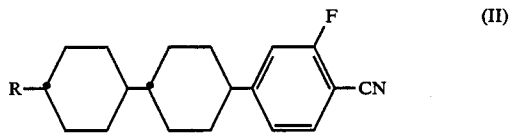

wherein R is as defined above, exhibit a liquid crystal phase within a broad mesomorphic range up to high temperatures. Further, compounds of the formula (I) wherein X represents COCH$_3$ have a low viscosity although their $\Delta\epsilon$ values are small. Particularly, compounds of the formula (I) wherein X represents COCH$_3$ and n is 2 exhibit a liquid crystal phase in a broad temperature range. Further, compounds of the formula (I) wherein X represents COCH$_3$ are obtained as intermediate compounds in the preparation of compounds of the formula (I) wherein X represents CN, as described later.

Next, preparation of compounds of the present invention will be described.

A 1-fluoro-3-(4-substituted cyclohexyl)benzene (a compound of the formula (II) wherein n is 1) or a 1-fluoro-3-[trans-4-(trans-4-substituted cyclohexyl)cyclohexyl]benzene (a compound of the formula (2) wherein n is 2), prepared according to a known method (e.g. a method described in U.S. Pat. No. 4,405,488), is reacted with acetyl chloride in the presence of aluminum chloride using $CS_2$ solvent to obtain a 2-fluoroacetophenone derivative (3) corresponding to the formulas (IV) and (V) of claimed compounds. This derivative is then reacted with sodium hypobromite in dioxane to obtain a carboxylic acid compound (4) which is then reacted with thionyl chloride in toluene to obtain an acid chloride compound, which is then reacted with an aqueous ammonia to obtain an acid amide compound (5), which is then dehydrated with thionyl chloride to obtain the objective 3-fluoro-4-cyano-1-(trans-4-substituted cyclohexyl)benzene (III) or a 3-fluoro-4-cyano-1-[trans-4'-(trans-4-substituted cyclohexyl)cyclohexyl]benzene (II).

The foregoing is illustrated by the following chemical formulas:

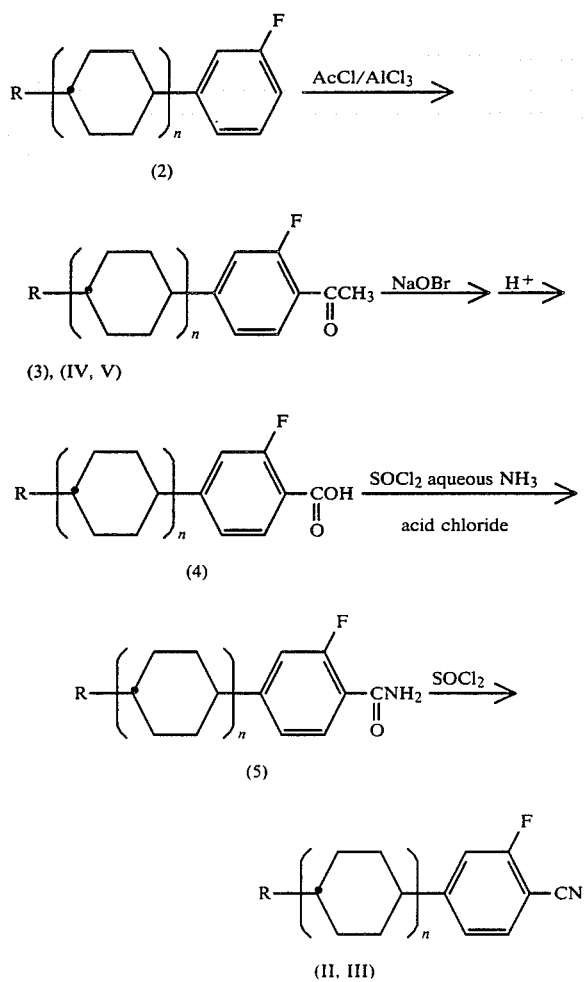

The present invention will be further described in detail by way of Examples.

EXAMPLE 1

Preparation of 2-fluoro-4-(trans-4-heptylcyclohexyl)acetophenone (a compound of the formula (I) wherein X represents $COCH_3$ and n is 1, i.e. a compound of the formula (V) wherein R represents $C_7H_{15}$)

1-Fluoro-3-(4-heptylcyclohexyl)benzene (18 g) was dissolved in $CS_2$ (50 ml), and aluminum chloride (7.2 g) was then dissolved in the solution, followed by adding acetyl chloride (5.3 g) with stirring at 2° to 5° C. for 10 minutes, gradually raising the temperature up to 35° C., keeping this temperature for 2 hours, cooling the mixture, adding 6N hydrochloric acid (50 ml), subjecting the resulting oil layer to extraction with toluene (100 ml), washing the solution with water till the washing liquid became neutral, distilling off the solvent under reduced pressure and recrystallizing the residue from ethanol to obtain the objective 2-fluoro-4-(trans-4-heptylcyclohexyl)acetophenone (yield: 9 g). This product was of a monotropic liquid crystal and exhibited a melting point (C-I point) of 35.6–40.2° C. and a nematic-clearing point (N-I point) of 21.5° C.

The following compounds were prepared in the same manner as above:

2-fluoro-4-(trans-4-propylcyclohexyl)acetophenone m.p. 63.3°–64.7° C.

2-fluoro-4-(trans-4-butylcyclohexyl)acetophenone m.p. 73°–77° C.

2-fluoro-4-(trans-4-pentylcyclohexyl)acetophenone m.p. 10.1°–13.5° C.

2-fluoro-4-(trans-4-hexycyclohexyl) acetophenone m.p. 58.2°–62.2° C.; N-I point 12.9° C.

EXAMPLE 2

Preparation of 1-cyano-2-fluoro-4-(trans-4-heptylcyclohexyl)benzene (a compound of the formula (I) wherein X represents CN and n is 1, i.e. a compound of the formula (III) wherein R represents $C_7H_{15}$)

Crystals of 2-fluoro-4-(trans-4-heptylcyclohexyl)acetophenone obtained in Example 1 (15 g) were dissolved in dioxane (50 ml) and cooled down to 10° C. or lower. Separately, sodium hydroxide (40 g) was dissolved in ice water (200 ml), and bromine (40 g) was dropwise added to the solution to obtain a solution of sodium hypobromite. This solution was dropwise added with stirring to the solution of the above compound, while keeping the temperature at 10° C. or lower, warming the mixture to 35° C. over 3 hours, allowing to stand overnight, adding 6N-hydrochloric acid (100 ml) for acidification, filtering the mixture to recover the precipitate and recrystallizing it from acetic acid (20 ml) to obtain crystals of 2-fluoro-4-(trans-4-heptylcyclohexyl)benzoic acid (4).

Crystals of this compound (4) (12 g) were suspended in toluene (20 ml), followed by adding thionyl chloride (5.9 g) to the suspension, reacting them at 70° C. for 6 hours, distilling off excess thionyl chloride under reduced pressure, pouring a residual oily substance in an aqueous ammonia (50 ml), recovering the resulting precipitate by filtration, and recrystallizing it from toluene to obtain crystals of 2-fluoro-4-(trans-4-heptylcyclohexyl)benzoic acid amide (5). The crystals (1.5 g) were dissolved in a mixture of toluene (50 ml) with dimethylformamide (50 ml), followed by adding thionyl chloride (5 g), subjecting the mixture to dehydration reaction at 80° C. for 5 hours, cooling the resulting material, adding ice water (50 ml), subjecting it to extraction with toluene (200 ml), distilling off the resulting oily substance under reduced pressure, filtering off insoluble matters, putting the filtrate in a refrigerator for crystallization, and recrystallizing the resulting crystals from n-heptane to obtain crystals of 1-cyano-2-fluoro-4-(trans-4-heptylcyclohexyl)benzene (yield: 0.2 g). The crystals exhibited a C-N point of 19.6°–20.9° C. and a N-I point of 21.2° C.

Compounds of the formula (III) containing other substituents were obtained in the same manner as above.

EXAMPLE 3

Preparation of 4-[trans-4-(trans-4-propylcyclohexyl)-cyclohexyl]-2-fluoroacetophenone (a compound of the formula (I) wherein X represents $COCH_3$ and n is 2, i.e. a compound of the formula (IV) wherein R represents $C_3H_7$ 3-[Trans-4-(trans-4-propylcyclohexyl)cyclohexyl]-fluroobenzene (5 g) was dissolved in $CS_2$ (50 ml), followed by adding aluminum chloride (4 g), dropwise adding acetyl chloride (3 g) with stirring at 5° C. or lower, raising the temperature up to 35° C., agitating the mixture for 2 hours, adding cold hydrochloric acid, subjecting the resulting precipitate to filtration and washing with ice water, and recrystallizing it from a mixed solvent of acetone with toluene to obtain the objective 4-[trans-4-(trans-4-propylcyclohexyl)cyclohexyl]-2-fluoroacetophenone (yield: 18%). It exhibited a C-N point of 88°–90° C. and a N-I point of 293° C.

4-[Trans-4-(trans-4-butylcyclohexyl)cyclohexyl]-2-fluoroacetophenone was obtained in the same manner as above. It exhibited a C-N point of 50°–53.5° C. and a N-I point of 123° C.

EXAMPLE 4

Preparation of 3-fluoro-4-cyano-1-[trans-4-(trans-4-propylcyclohexyl)-cyclohexyl]benzene (a compound of the formula (I) wherein X represents CN and n is 2, i.e. a compound of the formula (II) wherein R represents $C_3H_7$)

4-[Trans-4-(trans-4-propylcyclohexyl)cyclohexyl]-2-fluoroacetophenone (0.7 g) was suspended in dioxane (50 ml), followed by keeping the suspension at 10° C. or lower, dropwise adding to it with stirring, a solution of sodium hypobromite prepared by adding bromine (1.6 g) to sodium hydroxide (2 g) and ice water (30 ml), raising the temperature up to 35° C., continuing agitation for 5 hours, cooling the resulting material, acidifying it with 6N-hydrochloric acid, and subjecting the precipitate to filtration and water-washing to obtain 4-[trans-4-(trans-4-propylcyclohexyl)cyclohexyl]-2-fluorobenzoic acid, which was then recrystallized from acetic acid and dried. The product (0.6 g) was dissolved in toluene (20 ml), followed by adding thionyl chloride (2 g), refluxing the mixture for 3 hours, distilling off excess thionyl chloride under reduced pressure, pouring the resulting residual oily substance in an aqueous ammonia, filtering and water-washing the resulting precipitate, and recrystallizing it from toluene to obtain 4-[trans-4-(trans-4-propylcyclohexyl)cyclohexyl]-2-fluorobenzoic acid amide. This product (0.4 g) was dissolved in dimethylformamide (10 ml) and toluene (10 ml), followed by adding thionyl chloride (2 g), refluxing the mixture for 4 hours, cooling it, adding cold water, subjecting the mixture to separation and extraction with toluene (50 ml), water-washing the resulting oily layer till the washing liquid became neutral, distilling off toluene under reduced pressure, and recrystallizing a remaining oily substance from a mixed solvent of toluene with acetone to obtain crystals of the objective 3-fluoro-4-cyano-1-[trans-4-propylcyclohexyl)cyclohexyl]benzene (yield: 0.1 g). This product exhibited a crystalline-smectic point of 53.8° C., a smectic-nematic point of 89.8° C. and a nematic-clearing point of 207° C.

3-Fluoro-4-cyano-1-[trans-4-(trans-4-substituted cyclohexyl)cyclohexyl]benzenes having other substituents were obtained in the same manner as above.

USE EXAMPLE 1

A liquid crystal composition (A) consisting of
trans-4-propyl-(4'-cyanophenyl)cyclohexane 24% by weight,
trans-4-pentyl-(4'-cyanophenyl)cyclohexane 36% by weight,
trans-4-heptyl-(4'-cyanophenyl)cyclohexane 25% by weight, and
trans-4-pentyl-(4"-cyanobiphenyl)cyclohexane 15% by weight, had a nematic temperature range of −10° C.−+72.1° C. and a viscosity at 20° C. of 28 cp. When the composition was sealed in a TN cell having a transparent electrode and a distance between the inner walls, of 10 νm, the cell exhibited a threshold voltage of 1.76 V and a saturation voltage of 2.40 V.

2-Fluoro-4-(trans-4-heptylcyclohexyl)acetophenone of Example 1 (5 parts by weight) was added to the above liquid crystal composition (A) (95 parts by weight). The resulting liquid crystal composition had a N-I point of 68.4° C., but its viscosity at 20° C. was 27 cp and when it was sealed in the above TN cell, the threshold voltage and the saturation voltage were 1.69 V and 2.32 V, respectively.

USE EXAMPLE 2

A liquid crystal composition consisting of the above liquid crystal composition (A) (90% by weight) and 1-cyano-2-fluoro-4-(trans-4-heptylcyclohexyl)benzene of Example 2 (10% by weight) had a N-I point of 66.3° C., a viscosity at 20° C. of 27 cp and a Δξ of 13.4, and when it was sealed in the above cell, the threshold voltage and the saturation voltage were 1.62 V and 2.24 V, respectively.

USE EXAMPLE 3

A liquid crystal composition (B) consisting of
trans-4-propyl-(4'-cyanophenyl)cyclohexane 28 by weight,
trans-4-pentyl-(4'-cyanophenyl)cyclohexane 42% by weight and
trans-4-heptyl-(4'-cyanophenyl)cyclohexane 30% by weight, exhibited a nematic temperature range of −3° C.−+52° C. The threshold voltage, the saturation voltage and the viscosity at 20° C. were 1.6 V, 2.2 V and 23 cp, respectively.

4-[Trans-4-(trans-4-propylcyclohexyl)cyclohexyl]-2-fluoroacetophenone of Example 3 (10 parts by weight) was added to the above liquid crystal composition (B) (90 parts by weight). The resulting liquid crystal composition exhibited a N-I point of 62° C., and its viscosity at 20° C. was 24 cp, i.e. almost unchanged.

Thus, when the compound of the present invention was added, it was possible to obtain a liquid crystal composition having a low viscosity and a high clearing point.

USE EXAMPLE 4

A liquid crystal composition consisting of the above liquid crystal composition (B) (90 parts by weight) and 3-fluoro-4-cyano-1-[trans-4-(trans-4-propylcyclohexyl)-cyclohexyl]benzene of Example 4 (10 parts by weight) had a N-I point of 66° C. and a Δε of +12.5, and when a TN cell was prepared in the same manner as above, the threshold voltage and the saturation voltage lowered down to 1.40 V and 1.90 V, respectively, and the viscosity increased up to 29 cp, but such an extent of value however is not practically a hindrance.

As described above, when the compound of the present invention is used, it is possible to reduce the operation voltage of display elements and also to broaden their operation temperature range.

What we claim is:

1. Fluorobenzene derivatives expressed by the general formula

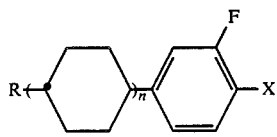

(I)

wherein X represents CN or COCH$_3$ and n is 2 when X is CN and n is 1 or 2 when X is COCH$_3$, and R represents hydrogen atom or an alkyl group of 1–15 carbon atoms or an alkoxy group of 1 to 15 carbon atoms.

2. A fluorobenzene derivative according to claim 1 wherein X is CN.

3. A fluorobenzene derivative according to claim 1 wherein X is COCH$_3$ and n is 2.

4. A flurobenzene derivative according to claim 1 wherein X is COCH$_3$ and n is 1.

5. A liquid crystal composition comprising two or more liquid crystalline components wherein at least one of the components is a fluorobenzene derivative expressed by the general formula

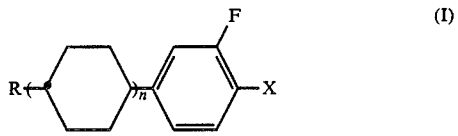

(I)

wherein X represents CN or COCH$_3$ and n is 2 when X is CN and n is 1 or 2 when X is COCH$_3$, and R represents hydrogen atom or an alkyl group of 1–15 carbon atoms or an alkoxy group of 1 to 15 carbon atoms.

6. A composition according to claim 5 wherein X is CN.

7. A composition according to claim 5 wherein X is COCH$_3$ and n is 2.

8. A composition according to claim 5 wherein X is COCH$_3$ and n is 1.

* * * * *